United States Patent
Nakao et al.

(10) Patent No.: US 7,462,649 B2
(45) Date of Patent: Dec. 9, 2008

(54) METHOD FOR RECYCLING PET BOTTLE

(75) Inventors: Takuo Nakao, Tochigi (JP); Tetsuya Chikatsune, Ehime (JP); Minoru Nakashima, Yamaguchi (JP); Minoru Suzuki, Ehime (JP); Hiroki Nagano, Ehime (JP)

(73) Assignee: Teijin Limited, Osaka (JP)

( * ) Notice: Subject to any disclaimer, the term of this patent is extended or adjusted under 35 U.S.C. 154(b) by 302 days.

(21) Appl. No.: 10/491,783

(22) PCT Filed: Oct. 16, 2002

(86) PCT No.: PCT/JP02/10754

§ 371 (c)(1),
(2), (4) Date: Apr. 6, 2004

(87) PCT Pub. No.: WO03/033581

PCT Pub. Date: Apr. 24, 2003

(65) Prior Publication Data
US 2005/0004390 A1 Jan. 6, 2005

(30) Foreign Application Priority Data

| Oct. 16, 2001 | (JP) | ............................. 2001-317559 |
| Oct. 16, 2001 | (JP) | ............................. 2001-317562 |
| Oct. 16, 2001 | (JP) | ............................. 2001-317884 |
| Nov. 27, 2001 | (JP) | ............................. 2001-306675 |
| Nov. 27, 2001 | (JP) | ............................. 2001-360674 |
| Nov. 27, 2001 | (JP) | ............................. 2001-360676 |
| Nov. 27, 2001 | (JP) | ............................. 2001-360677 |

(51) Int. Cl.
*C08J 11/22* (2006.01)
*C08J 11/24* (2006.01)

(52) U.S. Cl. ...................................... 521/48; 521/48.5
(58) Field of Classification Search .................. 521/48, 521/48.5; 528/275
See application file for complete search history.

(56) References Cited

U.S. PATENT DOCUMENTS

| 3,631,153 | A | * | 12/1971 | Carter et al. ................. 528/280 |
| 4,519,975 | A | | 5/1985 | Neumann |
| 4,609,680 | A | | 9/1986 | Fujita et al. |
| 4,644,049 | A | * | 2/1987 | Tung et al. ................... 528/272 |
| 5,262,460 | A | * | 11/1993 | Suzuki et al. ................ 524/135 |
| 5,830,981 | A | * | 11/1998 | Koreishi et al. .............. 528/283 |
| 5,952,520 | A | | 9/1999 | Naujokas |
| 6,136,869 | A | | 10/2000 | Ekart et al. |
| 6,162,837 | A | | 12/2000 | Gerking et al. |
| 6,472,557 | B1 | * | 10/2002 | Pell et al. ..................... 562/483 |
| 6,706,843 | B1 | * | 3/2004 | Ishihara et al. ................ 560/76 |
| 7,078,440 | B2 | * | 7/2006 | Ishihara et al. ................ 521/48 |
| 2002/0086970 | A1 | * | 7/2002 | Cho et al. ..................... 528/275 |

FOREIGN PATENT DOCUMENTS

| EP | 0 924 678 A2 | 6/1999 |
| EP | 1 227 075 A1 | 7/2002 |
| GB | 2 172 601 A | 9/1986 |
| JP | 43-2088 | 1/1968 |
| JP | 47-1616 B | 1/1972 |
| JP | 47-11983 B | 4/1972 |
| JP | 48-26748 B | 8/1973 |
| JP | 57-95925 A | 6/1982 |
| JP | 5-25867 B2 | 4/1993 |
| JP | 6-51810 B2 | 7/1994 |
| JP | 10-265561 A | 10/1998 |
| JP | 11-021374 A1 | 1/1999 |
| JP | 11-100350 | 4/1999 |
| JP | 11-302443 | 11/1999 |
| JP | 2000-169623 A | 6/2000 |
| JP | 2001-054911 | 2/2001 |
| JP | 2001-81175 A | 3/2001 |
| JP | 2002-167469 A | 6/2002 |
| WO | WO-00/47658 A1 | 8/2000 |
| WO | WO-01/30729 A1 | 5/2001 |

OTHER PUBLICATIONS

JPO machine translation of JP 2002-167469, abstract and pp. 1-7.*
Supplemental European Search Report dated Oct. 12, 2004.
English Translation of The International Preliminary Examination Report (Jul. 1, 2004).
International Search Report (English Translation).
Office Action mailed on Mar. 20, 2007 (Japan).

* cited by examiner

*Primary Examiner*—Katarzyna Wyrozebski
(74) *Attorney, Agent, or Firm*—Rader, Fishman & Grauer, PLLC

(57) ABSTRACT

A through process comprising depolymerization reaction of used PET bottles with EG, recovering DMT by ester interchange reaction with MeOH, obtaining terephthalic acid by hydrolysis of the recovered DMT, and manufacturing a PET polymer which can be used for manufacturing PET bottles again by using the terephthalic acid.

18 Claims, 1 Drawing Sheet

US 7,462,649 B2

METHOD FOR RECYCLING PET BOTTLE

TECHNICAL FIELD

The present invention relates to a method for obtaining a polymer for PET bottle again from resin bottle wastes containing polyethylene terephthalate (hereafter, this may be abbreviated as PET) as the main component. More specifically, the invention relates to a method carried out as follows: resin bottle wastes containing PET as the main component and further containing components different from PET are subjected to pretreatments of crushing, washing, removing foreign bodies etc.; the product is subjected to chemical reaction treatments to recover a high-purity dimethyl terephthalate (hereafter, this may be abbreviated as DMT) as an effective component; terephthalic acid (hereafter, this may be abbreviated as TA) is obtained through chemical reactions from the recovered DMT; and further the terephthalic acid is converted to a PET polymer for PET bottles.

BACKGROUND ART

A polyalkylene terephthalate, especially PET is manufactured and used in large quantities in the fields of living related materials such as fiber, film and resin, food related materials such as bottles for drinking water and carbonated drinks, and others because of its excellent chemical stability.

However, the disposal of wastes of fiber, film and resin products, and off-specification PETs, which are largely generated with increasing manufacturing quantities and consumption quantities, is presently becoming large social issues. Regarding material recycling, chemical recycling, thermal recycling etc., various methods have been proposed.

On the other hand, although especially the disposal of PET, bottles among the wastes is becoming more serious due to bulkiness, only material recycling that recovered used PET bottles are remelted and fibers are produced from the molten matter, is realized as a recycling method. But, when melt molding is simply used, it is not possible to reuse as PET bottles because of the deterioration of physical properties.

Further, a refilling method that PET bottles are washed and refilled has issues regarding the following, that is, who paying the cost of recovery, the points of safety and hygiene, and limitation in the number of times of reusing. The PET bottles are ultimately disposed, and the method can not be an permanent countermeasure. Further, PET bottle wastes contain foreign resins represented by polystyrene (hereafter, this may be abbreviated as PS), polypropylene (hereafter, this may be abbreviated as PP) and polyethylene (hereafter, this may be abbreviated as PE) which are originated from PET bottle product-constituting materials, for example, labels, shrink films, base caps, caps or the like, foreign plastics such as polyvinyl chloride (hereafter, this may be abbreviated as PVC) and polyolefinic resins, aluminum derived from caps and aluminum cans, iron derived from steel cans, adhesives, pigments, dyes and others.

Even in a bale of PET bottles recovered through collection of classified refuse, the mixing of foreign materials is hardly avoided. Even in chemical recycling that PET bottles are decomposed to monomers constituting the PET polymer by using a solvent such as water, methanol (hereafter, this may be abbreviated as MeOH) or ethylene glycol (hereafter, this may be abbreviated as EG), and the monomers are reused, the foreign materials generate various decomposition gases (for example, hydrogen chloride gas etc.) and various decomposition products (for example, lower hydrocarbons etc.) in the courses of heating process and reaction process, or mixed materials themselves sometimes largely deteriorate the quality of the monomer (DMT) recovered by chemical reactions, or they melt and become solid in recovering apparatuses to damage machinery and tools.

The chemical recycling includes, for example, a method by which polyester wastes are hydrolyzed in the presence of an alkali compound to obtain TA described in JP-A 11-21374 (JP-A means Japanese unexamined patent publication) and a method by which DMT and EG are obtained by gas phase MeOH decomposition in MeOH described in U.S. Pat. No. 5,952,520.

However, since these processes all need a reaction condition of high temperature of 200° C. or higher, they have very low allowance against the mixing of foreign plastics which start to decompose from the temperature of 190° C., for example, PVC and whose decomposed products cause quality deterioration of the final product.

Further, JP-A 2000-169623 describes a process in which PET wastes are decomposed with EG, the recovered bis-β-hydroxyethyl terephthalate (hereafter, this may be abbreviated as BHET) is purified by a thin-film evaporator, and subsequently the BHET is subjected to melt polycondensation to obtain PET polymer. However, this process also has a step imposing a heat history of 200° C. or higher, and the allowance of mixing of heat-decomposable foreign plastics such as PVC is small.

Namely, although chemical recycling has an allowance of the mixing of impurities larger than that of material recycling, it is required to remove the impurities almost completely in pretreatment processes. Further, it is generally known that the PET polymer for bottles is manufactured by obtaining an oligomer through an ester interchange reaction or an esterification reaction of DMT or TA used as a starting material with EG followed by a polycondensation reaction which is carried out successively. In this case, the DMT or TA of the raw material should be highly purified, and the contents of impurities should be sufficiently little; and otherwise, the obtained PET polymer can not be used for PET bottles.

Due to the circumstances having above mentioned various restrictions, no process capable of recovering effective components from used PET bottles through a chemical recycling process and again obtaining a PET polymer usable for PET bottles has been reported.

DISCLOSURE OF THE INVENTION

The object of the present invention is to solve the above-mentioned problems of the conventional technologies and to propose a process that, even from used PET bottles containing impurities, a pollution-free high-purity monomer (DMT) can be obtained, and a PET polymer suitable for PET bottles can be manufactured effectively from the high-purity DMT.

BEST MODE FOR CARRYING OUT THE INVENTION

Figure 1:
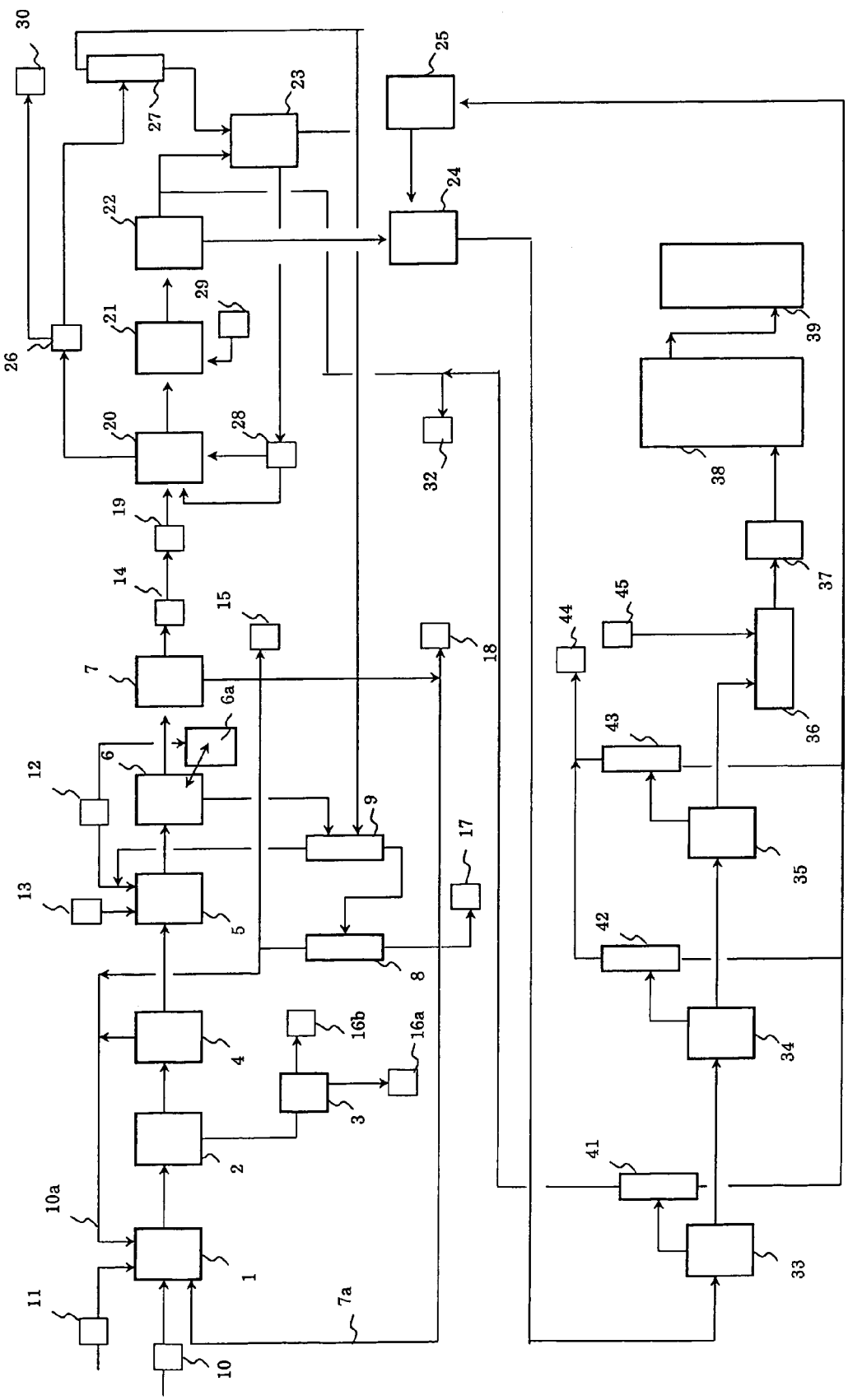
FIG. 1 is an outline drawing schematically exhibiting one mode of the method for recycling PET bottles in the present invention, for explaining the flow of the processes.

The method of the present invention, that is, a high-purity DMT is recovered as an effective component from wastes of resin bottles containing PET as the main component and further containing components different from it, TA is obtained through chemical reactions, and further a PET polymer for PET bottles is obtained, is characterized in that the resin bottle wastes are treated in such a manner that the following Processes (1) to (17) are passed sequentially.

(1) A process for unpacking a packed bale of PET bottles which have been recovered through collection of classified refuse.
(2) A process for removing iron and aluminum by a metal detector from the unpacked PET bottles, and subsequently crushing the PET bottles into flakes of 2-30 mm in sizes.
(3) A process for separating polymer components different from PET, of labels (thin film) and consisting of PE, PS, PVC or the like from flaky pieces of PET bottles by winnowing.
(4) A process for washing and gravity sorting which has both the roles of washing out foreign materials attached inside and outside the crushed bottle pieces and/or residues of the contents inside the PET bottles with water, and further removing sands and stones having specific gravities larger than water and PET, and foreign plastics such as PE and PP having specific gravity smaller than water.
(5) A depolymerization process for producing BHET by charging recovered PET flakes into EG containing a PET depolymerization catalyst and treating the mixture at 175-190° C. under a pressure of 0.1-0.5 MPa.
(6) A solid-liquid separation process for removing solid foreign materials which have not dissolved in the above reaction solution.
(7) A BHET concentration process for distilling and concentrating the solution fraction which has passed the solid-liquid separation process.
(8) An ester interchange-recrystallization process for forming crude DMT and EG through an ester interchange reaction of the concentrated BHET in MeOH in the presence of an ester interchange reaction catalyst, and subjecting the reaction mixture to recrystallization in a MeOH solvent.
(9) A DMT distillation process for removing MeOH by distillation from the DMT cakes to purify the DMT.
(10) A hydrolysis process for subjecting the purified DMT obtained in the DMT distillation process to a hydrolysis reaction together with water at 230-250° C. to produce TA.
(11) A process for cooling an aqueous slurry of the TA obtained in the hydrolysis process.
(12) A process for obtaining TA cakes from the cooled aqueous slurry of TA through solid-liquid separation.
(13) A slurry adjusting process for mixing the TA cakes with EG, and adjusting the mole ratio of TA/EG to 1:1 to 1:3.
(14) A process in which TA and EG are made to perform an esterification reaction to obtain a PET oligomer.
(15) An initial melt-polycondensation process in which a polycondensation catalyst and a stabilizer are added to the PET oligomer, the mixture is subjected to a melt polycondensation reaction in a weak vacuum of 1.3 kPa to 4.0 kPa at 260-300° C. to remove EG, and thus the degree of polymerization is increased.
(16) A latter term melt-polycondensation process in which the product of the previous process is further subjected to a melt polycondensation in a high vacuum of 67 Pa to 0.7 kPa at 270-300° C. to remove EG by distillation, and thus the degree of polymerization is further increased.
(17) A solid phase polymerization process for increasing the degree of polymerization in order to obtain a PET suitable for bottles.

Hereafter, the present invention will be explained process by process. In the present invention, Processes (1) to (4), which precedes the processes accompanied by chemical reactions, are called pretreatment processes. In the pretreatment processes, a packed bale of PET bottles which have been recovered through collection of classified refuse is unpacked, and subsequently, iron and aluminum are removed. These metals can be easily removed by using a metal detector. Subsequently, the recovered PET bottles are crushed into pieces of 2-30 mm in sizes. The sizes of crushed pieces are more preferably 2-20 mm. By this treatment, the depolymerization reactivity is improved, and the performance for treating PET bottle wastes is increased. This effect is especially significant for the thick parts which have been treated for crystallization and whitening in order to increase the strength and stabilize the size of PET bottles. The crushed products often contain foreign plastics different from polyester such as PE, PP, PS and PVC, which are materials of caps or labels contained in the polyester resin as impurities.

In the present invention, to cope with the mixing of the above-mentioned foreign plastics, reaction conditions are selected so that they are decomposed in the later reaction processes, and the purity of the recovered monomer is not lowered; however, there remains such a possibility that the foreign plastics have undesirable influences on handling, for example, they may stick on reactors, cause clogging on a filter and so on. Accordingly, to promote the reactions smoothly, it is important to remove the foreign plastics in the pretreatment processes, and suppress their mixing into the reaction processes as far as possible.

However, it is not necessary for the present invention to include various processes to completely remove the above-mentioned foreign plastics, which is the case of material recycling, but only processes of necessity minimum are required.

In order to remove thin films (PE, PP, PS, PVC etc.) used in labels etc. and different than polyester, from the above crushed products, at first, winnowing is used to remove labels. When the air volume is too large, the useful component of polyester resin is removed together, and accordingly the air volume should be controlled. By the winnowing, labels mainly comprising PP, PS or PVC can be removed almost completely.

Subsequently, in order to remove caps composed mainly of PE, which can not be removed by winnowing, the crushed material is treated by a gravity sorter. The foreign plastics such as PP and PE having a specific gravity lighter than water are removed by the gravity sorting to obtain recovered flakes.

Since the above-mentioned gravity sorter works also as an apparatus for washing out the impurities originated from foods (refreshing drink, soy sauce or the like) attached and remained on polyester resin or the like with water, there is no problems even in the case where contents remain inside the resin. The wash water separated by a centrifuge is recycled to the gravity sorter again, and a part is purged and treated as wastes. Further, sands and stones having specific gravity extremely larger than the specific gravities of water and PET are removed by the sedimentation on the bottom of the water washing machine.

The recovered flakes which have been discharged from the gravity sorter are transported by pneumatic transportation to a reactor in a reaction process via a flake storing tank. In the case where the sizes of the flakes after crushing are specified at a relatively large range of 30-150 mm in the above-mentioned crushing process, the transportation efficiency in the pneumatic transportation process becomes poor, and problems of the clogging of a rotary valve and the like may occur, and accordingly, it is effective to crush to about 2-30 mm in sizes like the present invention.

Further, on the recovered flakes before the pneumatic transportation, the water used in centrifugal operation with a decanter remains in an amount of about 0.5 wt. % based on the weight of the recovered flakes. Water exerts unfavorable influences on the reaction velocity in the depolymerization process, but the remaining water is dried during the pneumatic transportation, and the water content is lowered down to 0.1 wt. % or less based on the weight of the recovered flakes finally, and thereby there is no problem in the progress of the reaction.

In the above-mentioned pretreatment processes, most of the components other than polyester can be removed, that is, the pretreatment is completed with widely smaller number of processes than in the case of material recycling. This is because that, if impurities remain, they can be removed in the later processes through physical and chemical separation methods. Further, in the material recycling, colored bottles become impurity, and they must be removed by a sorter, but in the method of the present invention, the pigments contained in the colored bottles also can be removed in later reaction processes, and the bottles can be recycled as useful resource.

Next, the depolymerization catalyst to be used in Process (5) contains at least one kind of metal compound selected from a group consisting of carbonate salts, hydrogencarbonate salts, hydroxides, and alkoxides, each of an alkali metal, and carbonate salts, hydrogencarbonate salts, hydroxides, and alkoxides, each of an alkaline earth metal, and manganese acetate and zinc acetate. The quantity of the addition of the depolymerization catalyst is preferably 0.1 to 10 wt. % based on the weight of the PET flakes supplied to Process (5). Further, the quantity of EG to be used in Process (5) is preferably 0.5 to 20 times the quantity of the PET flakes supplied to Process (5) by weight. The reaction is preferably carried out under reaction conditions of a temperature of 175 to 190° C., and a pressure of 0.1 to 0.5 MPa. Thus, BHET is obtained.

Further, in Process (6), the solid foreign materials which did not dissolve in the reaction solution is removed by a solid-liquid separation.

In Process (7), the water component in the crude BHET generated as a by-product in the depolymerization reaction is mainly removed by distillation. In the process, the distillation-condensation operation is carried out preferably under a pressure of 1.3 to 133 kPa.

The ester interchange reaction catalyst to be used in Process (8) contains at least one kind of metal compound selected from a group consisting of carbonate salts, hydrogencarbonate salts, hydroxides and alkoxides of an alkali metal, carbonate salts, hydrogencarbonate salts, hydroxides and alkoxides of an alkaline earth metal, manganese acetate and zinc acetate, and the quantity of the addition of the catalyst is preferably 0.1 to 10 wt. % based on the weight of the PET flakes supplied to Process (5). Further, the quantity of MeOH to be used in Process (8) is preferably 0.5 to 20 times the quantity of the PET flakes supplied to Process (5) by weight. The reaction is preferably carried out under reaction conditions of a temperature of 65 to 85° C., and a pressure of 0,1 to 0.3 MPa.

In Process (9), mainly MeOH is distilled out from the obtained DMT cake to purify the DMT.

In Process (10), water is supplied in an amount of 0.5 to 5 times, preferably 0.8 to 1.2 times the weight of the DMT, and the reaction is carried out preferably at a temperature of 230 to 270° C.

An aqueous slurry of the TA which is obtained by cooling the reaction mixture of the above process is prepared in Process (11); and the slurry is subjected to a solid-liquid separation process for dehydration, and a water-containing TA cake having a water content of preferably about 10 to 20 wt. % is separated and recovered in Process (12).

EG is added to the obtained water-containing TA cake in such a manner that the molar ratio of TA/EG becomes 1:1 to 1:3 to prepare a slurry in Process (13). The content of water in the slurry is preferably in the range of 0,1 to 20 wt. % based on the weight of EG.

In stead of the above Process (13), the following Processes (13a) to (13b) may be passed before advancing to Process (14).

Process (13a): the TA cake obtained in Process (12) is treated by a dryer such as a vibrating fluid bed-type dryer or an inert gas flow-type dryer to obtain TA powder having water content of 0.5 wt. % or less.

Process (13b): the TA powder obtained in Process (13a) is placed into a slurry preparation tank, EG is charged so that the molar ratio of TA/EG becomes 1:1 to 1:3, and thus, a slurry is prepared.

But, in the case of passing through Processes (13a) and (13b), a large quantity of energy is consumed to dry the water in the TA cake, and accordingly, the mode passing Process (13) is better than that passing Processes (13a) and (13b).

Further, it is preferable that the TA obtained through the hydrolysis of DMT is slurried in EG in a state where a small amount of water remains in it because this increases handleability. The water content in the EG slurry of TA is preferably in the range of 0,1 to 20 wt. % based on the weight of EG, especially preferably 1 to 5 wt. %.

In Process (14), when TA and EG are subjected to an esterification reaction to obtain a PET oligomer, the esterification temperature is preferably 260 to 270° C.

In Process (15), the polycondensation reaction catalyst to be added to the PET oligomer is selected from a group consisting of germanium, antimony and titanium compounds represented by germanium oxide, antimony trioxide and titanium trimellitate, and the addition quantity is preferably 0.002 to 0,1 wt. % based on the weight of TA supplied to Process (13). Further, a stabilizer to be added is preferably a phosphoric ester such as trimethyl phosphate, triethyl phosphate or triphenyl phosphate, a phosphorous ester such as triphenyl phosphite or trisdodecyl phosphite, an acidic phosphoric ester such as methyl acid phosphate, dibutyl phosphate or monobutyl phosphate, or a phosphorus compound such as phosphoric acid, phosphorous acid, hypophosphorous acid or polyphosphoric acid. The reaction conditions are preferably a temperature of 260 to 300° C. and a weak vacuum of 1.3 kPa to 4.0 kPa.

In Process (16), the reaction conditions are preferably a temperature of 270 to 300° C. and a strong vacuum of 67 Pa to 0.7 kPa.

In Process (17), the solid phase polymerization reaction, which adjusts the degree of polymerization and decreases the content of cyclic oligomers, acetaldehyde etc., may be carried out either in a nitrogen stream or in a vacuum.

Hereafter, the present invention will be explained further in detail by using FIG. 1, which shows one mode of the method of recycling of PET bottles in the present invention.

Recovered PET bottle flakes which have been treated in the pretreatment processes (not shown in the figure) of Processes (1) to (5), a depolymerization reaction catalyst and further EG are charged concurrently into a depolymerization tank (1 in the figure) from a supply source (11 in the figure), a supply tank (10 in the figure) and a supply line (10a in the figure), respectively, and the PET flakes are depolymerized in the depolymerization tank (1 in the figure).

The depolymerized mixture is sent to a solid-liquid separation apparatus (2 in the figure). The components which do not dissolve in the depolymerization tank (1 in the figure) are separated by the solid-liquid separation apparatus (2 in the figure), and they are removed outside the system as solid materials. The solid materials are further washed with EG in a washing tank (3 in the figure), and the materials attached on the solid materials are recycled to the depolymerization tank (1 in the figure) if required. The solid materials themselves are removed into a solid material tank (16b in the figure) separately. Preferably, the retention time in the depolymerization tank (1 in the figure) is 1 to 10 hr, and the inner temperature is 175 to 190° C.

Subsequently, the depolymerization reaction product after the completion of the depolymerization is sent to a distillation-concentration tank (4 in the figure), and EG is removed by distillation so that the ratio of EG to the depolymerization reaction product becomes 0.5 to 2.0 in terms of a charged weight ratio in the next process. The removed EG can be recycled to the depolymerization tank (1 in the figure).

Subsequently, the concentrated liquid of the depolymerization reaction product is fed to an ester interchange reaction tank (5 in the figure), and an ester interchange reaction catalyst and MeOH are-fed from an ester interchange reaction catalyst supply source (13 in the figure) and a MeOH supply source (12 in the figure), respectively. Thus, the depolymerization reaction product is converted to DMT and EG. It is preferable to carry out the reaction in the ester interchange tank at the inner temperature of 65 to 85° C., the inner pressure of 0,1 to 0.3 MPa and the retention time of 0.5 to 5 hr. After adding an excess amount of MeOH, the obtained mixture of DMT and EG is cooled, and the mixture is treated by a solid-liquid separation apparatus (6 in the figure) to produce DMT cakes, and a mixture of EG and MeOH.

Since the separated DMT cakes contain MeOH as a mother liquid, they are slurried again in MeOH, and subjected to solid-liquid separation. Further, the DMT cakes are supplied to a DMT distillation tower (7 in the figure), and the purified DMT is collected in a DMT recovery tank (14 in the figure). A part of the residual liquid on the bottom of the distillation tower (7 in the figure) is returned to the depolymerization tank (1 in the figure) through a line (7a in the figure), and the rest is disposed to the outside (18 in the figure) of the system.

On the other hand, the mixed liquid of EG and MeOH obtained by the solid-liquid separation is supplied to a MeOH rectification tower (9 in the figure), and MeOH is distilled out. The distilled-out MeOH can be used as a part of the MeOH which is supplied to the ester interchange reaction tank (5 in the figure). Further, the residual liquid on the bottom of the MeOH rectification tower (9 in the figure) is supplied to an EG distillation tower (8 in the figure) to distill out EG. A part of the distilled-out EG is recycled as the EG supplied to the depolymerization tank (1 in the figure) through the line (10a in the figure), and the excess EG is collected and taken out to the outside (15 in the figure) of the system.

Furthermore, a part of the residual EG of the EG distillation tower (8 in the figure) is returned to the depolymerization tank (1 in the figure) and the rest is taken out to the outside (17 in the figure) of the system as a waste.

Continuously, the process for obtaining TA by subjecting the DMT to a hydrolysis reaction will be explained by using FIG. 1.

The DMT which has been purified and is stored in the DMT recovery tank (14 in the figure) is heated up as in a molten state to the hydrolysis reaction temperature in a DMT heater (19 in the figure). The heated DMT is supplied to a hydrolysis reaction tank (20 in the figure) together with hot water which has been heated in a water boiler (28 in the figure). The weight ratio of the water/DMT supplied to the reaction tank is preferably in the range of 1:0.5 to 1:4. The reaction temperature and the reaction pressure in the reaction tank are preferably 230 to 250° C., and 2.9 to 4.0 MPa (gauge pressure), respectively. The hydrolysis reaction is an equilibrium reaction, and a high reaction rate can be realized by effectively removing the byproduced MeOH in the reaction. Accordingly, as a heat source for quickly removing the MeOH and keeping the reaction temperature, high-pressure steam generated in the water boiler (28 in the figure) is introduced into the reaction vessel. The MeOH byproduced in the hydrolysis reaction and the entrained water are removed from the upper part of the reaction tank. It is preferable that the weight of the steam introduced from the water boiler is equal to that of the water taken out from the upper part of the reaction tank. The retention time in the hydrolysis reaction tank is preferably 1 to 5 hr.

Next, the hot TA/water slurry obtained in the hydrolysis reaction tank (20 in the figure) is supplied to a cooling tank (21 in the figure) for cooling it. In the cooling tank, the slurry receives quick pressure change, and the water in the slurry is vaporized. In order to make up for the deficiency of water due to the vaporization and its consumption by the reaction, water is supplied from a water supply tank (29 in the figure). The water to be supplied is preferably ion-exchanged pure water in order to prevent the contamination of the product by impurities. Further, it is preferable to use the water whose dissolved air, especially oxygen has been removed in order to prevent the erosion of equipments including the hydrolysis reaction tank.

The cooled TA/water slurry is supplied to a solid-liquid separator (22 in the figure), and it is separated into TA cakes and water. The TA cakes obtained by the solid-liquid separator are supplied to a slurry preparation tank, and a slurry having a molar ratio (EG/TA) of 1:1 to 1:3 is prepared with EG supplied from an EG supply source (25 in the figure).

The mixed vapor of water/MeOH generated from the hydrolysis reaction tank (20 in the figure) is condensed by a steam condenser (26 in the figure), subsequently it is separated by distillation to MeOH and water with a MeOH distillation tower (27 in the figure), the MeOH obtained from the top of the distillation tower is supplied to the above-mentioned MeOH rectification tower (9 in the figure), and it is treated by distillation again. Further, the water obtained from the bottom of the MeOH distillation tower (27 in the figure) is sent to a water supply tank (23 in the figure), heated in the water boiler (28 in the figure) and recycled to the hydrolysis reaction tank (20 in the figure) again.

A part of the MeOH byproduced in the hydrolysis reaction becomes dimethyl ether (hereafter, this may be abbreviated as DME) through dehydration reaction. The DME is sent to a waste gas treating apparatus (30 in the figure) from a steam condenser (26 in the figure) in gas as it is and subjected to incineration disposal.

Further, the water separated by the solid-liquid separator (22 in the figure) is mostly sent to the water supply tank (23 in the figure) to recycle and partly sent to a waste-water treatment facility (32 in the figure) as waste water.

Successively, the processes for obtaining a PET polymer from the obtained TA slurry will be explained by using FIG. 1.

The TA/EG slurry whose mole ratio has been adjusted in a TA slurry tank (24 in the figure) is supplied to an esterification tank (33 in the figure), and a PET oligomer is obtained through an esterification reaction. Preferably, the reaction temperature of the esterification tank (33 in the figure) is 260 to 270° C. and the retention time is 1 to 5 hr.

During the reaction, the reaction product mixture of EG/water is distilled out, and the distillate is separated to EG and water by an EG distillation tower (41 in the figure). The EG is redistilled by an EG distillation tower (30 in the figure), and further redistilled by the EG distillation tower (8 in the figure).

The PET oligomer obtained in the esterification tank (33 in the figure) is supplied to an initial polycondensation reaction tank (34 in the figure) after the addition of germanium dioxide as a catalyst and trimethyl phosphate as a stabilizer, and a polycondensation reaction is carried out under conditions of a weak vacuum of 1.3 to 4.0 kPa generated by a vacuum apparatus (44 in the figure) and a temperature of 260-300° C. Further, the obtained initial polycondensation product is supplied to a latter-term polycondensation reaction tank (35 in the figure), and a polycondensation reaction is carried out in a high vacuum of 67 Pa to 0.7 kPa generated by the vacuum apparatus (44 in the figure) at 270 to 300° C. Both the EG fractions byproduced in polycondensation reactions in the initial polycondensation reaction tank (34 in the figure) and the latter-term polycondensation reaction tank (35 in the figure) are subjected to distillation treatments in the EG distillation tower (8 in the figure) via the EG tank (30 in the figure).

The PET polymer obtained in the latter-term polycondensation reaction tank (35 in the figure) is taken out from it in a plate or strand, and cooled in a cooling bath (36 in the figure). Then, it is cut by a cutter (37 in the figure) into pellets. In order to adjust the degree of polycondensation of the PET polymer at the specific level suitable for PET bottle, the obtained PET pellets are treated for a polycondensation reaction in a pellet state in a solid phase polymerization tank (38 in the figure) furnished with a dryer and a preliminary crystallizer. The polycondensation reaction can be carried out either in a vacuum or in nitrogen stream. The final PET product is stored in a storage tank (39 in the figure). The PET polymer is used as a polymer suitable for PET bottles.

Further, the wastes of PET oligomers and PET polymers which are generated from the initial polymerization tank, the latter-term polymerization tank and the solid-phase polymerization tank, can be supplied directly to the depolymerization reaction tank to depolymerize them, or they are supplied to a crusher, and after crushing, they are supplied to the depolymerization reaction tank, depending on their forms. Thus, the losses of wastes in a series of the processes can be made as little as possible, and the wastes can be recycled. Further, considerable parts of the water, EG and MeOH generated in every process can be recycled to any process in a series of the processes by subjecting them to a distillation treatment in advance. Accordingly, the wastes can be recycled with the loss suppressed as far as possible.

EXAMPLES

The present invention will be explained further in detail hereafter with examples, while the present invention is not restricted by the examples. Further, each value in the examples was obtained in accordance with the following methods.

1. Analysis of DMT (1)

(1) Chlorine Content in DMT

A DMT sample was dissolved in MeOH, and the chlorine concentration was determined by using a chlorine-sulfur analyzer/total-organic halogen analyzer ("TOX 100" manufactured by Mitusi Chemical) on the basis of the mixture whose chlorine content had been determined in advance.

(2) Organic Impurities in DMT

A DMT sample was subjected to recrystallization treatments by using an acetone solvent and a MeOH solvent, and the collected solvents were concentrated. The impurities in the concentrate were determined by gas chromatography (instrument: HP 5890 manufactured by Hewlett-Packard; capillary column: DB-17 manufactured by J&W) using an acetone solvent of a guaranteed grade as the sample solvent.

2. Analysis of Terephthalic Acid (3) 4-CBA and p-TA

A TA sample was dissolved in 2N-ammonia water, and 4-CBA and p-TA were separately determined on a liquid chromatograph system (LC-6A manufacturing by Shimazu) with STR φ DS-H column.

(4) Weight Concentration of MMT and DMT

These were determined by high-speed liquid chromatography (instrument: HPLC D-7000 manufactured by Hitachi; filled column: RP-18, 2 pieces).

(5) Weight Concentration of BA

A TA sample was esterified with diazomethane, and the esterified sample was analyzed on a gas chromatograph using a separation column of 10% SE-30 with an inner standard of n-tridecane.

(6) 250° C. Heat-resistant Alkali Permeability

After held for 2 hr at 250° C., a TA sample was dissolved in a 2N-potassium hydroxide solution, and the UV-permeability of the solution at 400 nm in wave length was determined by a spectrophotometer (an instrument equivalent to UVIDEC 660 manufactured by Nippon Bunkou).

3. Analysis of PET (7) Intrinsic Viscosity

According to a conventional method, a sample was taken out from a chip or a molded body, a certain amount of the sample was weighed out, it was dissolved in o-chlorophenol so that it became 0.012 g/ml in concentration, the viscosity of the solution was determined with an Ostwald viscometer at 35° C. after the solution was once cooled, and the intrinsic viscosity was calculated from the viscosity.

(8) Haze

A sample was cut out in a size of 50 mm×50 mm from the body part of a PET bottle. Haze was determined on the sample by using a color and color difference meter (MODEL 1001 DP) manufactured by Nippon Denshoku.

(9) Content of Acetaldehyde

The content of acetaldehyde (hereafter, this is abbreviated as AA) was determined by freezing and crushing a sample, charging the crushed product into a vial, holding it for 60 min at 150° C., and analyzing the gas in the vial by using a head-space gas chromatograph manufactured by Hitachi.

(10) Content of Diethylene Glycol

A sample was decomposed with hydrazine hydrate and analyzed by a gas chromatograph ("263-70" manufactured by Hitachi).

(11) Content of Oligomer (Cyclic Trimer)

A sample was crushed with a crusher, a certain amount of the crushed product was weighed out, it was once dissolved in a small amount of a mixed solvent of hexafluoroisopropanone/chloroform, and subsequently the solution was diluted to a certain concentration (50 g/L) with chloroform. On this sample solution, a low molecular weight region was fractionated by gel permeation chromatography (GPC; ALC/GPC 244 manufactured by Waters), the corresponding peak was detected, and the amount of the oligomers in the sample was determined by using the peak based on a calibration curve prepared from a standard sample of the cyclic trimer.

Example 1

A bale (900 mm×1,000 mm×550 mm, and 120 kg) of PET bottles which had been recovered through collection of classified refuse was unpacked, iron and aluminum were removed by a metal detector, subsequently the materials were charged into a crusher, and a crushing operation was carried out with a screen whose aperture was set 10 mm. The crushed product was treated by a winnower to remove labels composed mainly of PE, PS and PP attached on bottles, subsequently, it was subjected to a washing-gravity separation process to washing out the content of bottles and at the same time to remove caps composed mainly of PP and PE, and the labels which was not removed by the winnowing, and thus, PET flakes were recovered. The recovered PET flakes were transported by pneumatic transportation to a recovered PET flake-supplying tank in order to store them in the tank. Subsequently, 100 pts. wt. of the recovered PET flakes, 360 pts. wt. of EG and further 2.7 pts. wt. of sodium carbonate were supplied to a depolymerization tank from the recovered PET flake-supplying tank, a EG supply line and a polymerization catalyst supplying tank, respectively. They were held for 4.5 hr at 180° C. under stirring.

The resulting solution of the depolymerization reaction with EG was charged into a filter having the periphery surrounded with heating units heated at 170° C. and furnished with a 100-mesh metal net as a filter medium, and filtered at a high temperature. The remaining materials on the filter medium was washed with 90 pts. wt. of EG heated at 170° C., and the washing was pooled in a washing reservoir.

The depolymerization reaction treatment solution obtained by the hot filtration was concentrated by reduced pressure distillation at 6.65 kPa, and 270 pts. wt. of EG was recovered as a distillate.

The resulting concentrate, and 2.7 pts. wt. of sodium carbonate from an ester interchange catalyst tank and further 180 pts. wt. of MeOH were charged into an ester interchange reaction tank, and they were held at a liquid temperature of 74° C. under normal pressure for 1 hr under stirring to carry out an ester interchange reaction. The resulting mixture of DMT, EG and MeOH was cooled to 40° C., and successively treated with a solid-liquid separator to obtain DMT cakes. The DMT cakes were once placed in a MeOH washing tank, 180 pts. wt. of MeOH was charged into it, the mixture was stirred at 40° C. to wash the DMT, the mixture was treated by the centrifugal separator to separate the solid portion from the liquid portion, and DMT cakes were again obtained. The obtained DMT cakes were again placed in the MeOH washing tank, and the DMT cakes were melted at 160° C. this time, and at the same time the residual MeOH was distilled out. The molten DMT was charged into a DMT distillation tower, DMT was distilled out as a distillate by a reduced pressure distillation at a pressure of 6.65 kPa to obtain 83 pts. wt. of a recovered DMT. The molten DMT was sent to a DMT recovery tank.

The DMT recovered by the process was a high purity DMT having a chlorine concentration of 1 ppm or less and a total amount of organic impurities of 100 ppm or less.

Subsequently, to a hydrolysis reaction tank were each continuously supplied the molten DMT from the DMT recovery tank at a speed of 100 pts. wt./hr, hot water from a water boiler at a speed of 100 pts. wt./hr and further high-pressure steam form the water boiler at 270° C. at a speed of 40 pts. wt./hr, respectively. The hydrolysis reaction was carried out under stirring by keeping the liquid temperature of the hydrolysis reaction tank at 250° C. and a retention time of 4 hr. The MeOH generated in the reaction was distilled out from the head of the reaction tank together with steam. The speed of the distillation was at about 400 pts. wt./hr as a mixed vapor of water and MeOH, and the inner pressure of the reaction tank during the reaction was about 4 MPa.

The aqueous slurry of the obtained TA was sent to a cooling tank at a speed of about 166 pts. wt./hr. The weight ratio of TA/water in the cooling tank was about 1/1. The TA/water slurry at about 250° C. was cooled down by a latent heat of vaporization of water due to flushing to atmospheric pressure, and the slurry was kept at about 100° C. Water in an amount equivalent to that vaporized during the cooling was fed to the cooling tank to keep the weight ratio of TA/water of the slurry in it at about 1/1.

From the cooling tank, the TA/water slurry was sent to a solid-liquid separator at a speed of 166 pts. wt./hr to obtain TA cakes. The weight ratio of TA/water of the obtained water-containing TA cakes was about 83:12. The water-containing cakes were sent to a slurry preparation tank in the next process in a wet state as it is.

In the obtained wet TA, the concentrations of DMT and MMT were 500 ppm and 50 ppm, respectively, and the total content of 4-CBA, p-TA and BA was 30 ppm. Further, the 250° C. heat-resistant alkali permeability was also 99.9% or more, and the TA was suitable as a raw material of PET for bottles.

Subsequently, a slurry consisting of 45 pts. wt. of the TA cakes (40 pts. wt. of TA and 5 pts. wt. of water) and 22 pts. wt. of EG was supplied to a polycondensation tank, and esterification reaction was carried out at 275° C. at atmospheric pressure for 4 hr. The byproduced water and the TA-entraining water were allowed to flow outside the system, and the esterification reaction was carried out to 97% in the esterification reaction rate to prepare an oligomer having a degree of polymerization of 5 to 10. Subsequently, 0.017 pt. wt. of a trimethyl phosphate solution in EG (5.5 mol % in terms of phosphorus atom) and 0.38 pts. wt. of a germanium dioxide solution in EG (1.0 mol % in terms of germanium atom) were added to the oligomer, and polycondensation was carried out for 1 hr under a reduced pressure of 2000 Pa and successively for 2 hr under a reduced pressure of 133 Pa and at 277° C.

The produced polymer was taken out in a form of strand from an exit formed on the bottom of the polycondensation tank in such a state that the exit was directly linked to a cooling water tank. After cooled with water in the tank, the strand was cut in chip-shape to obtain pellets. The obtained polymer pellets were crystallized in a stirring fluidized-type crystallizing machine followed by drying in nitrogen flow at 140° C. for 3 hr. Successively, they were transferred to a packed tower-type solid phase polymerizer and treated at 215° C. for 2 hr in nitrogen flow for solid phase polymerization to produce a chip-shaped polyethylene terephthalate resin.

The obtained chips had an intrinsic viscosity of 0.79, an AA content of 3.0 ppm and an oligomer content of 0.3 ppm.

Subsequently, after dried at 160° C. for 5 hr in a vacuum drier, the obtained chips were subjected to an injection molding to obtain a cylindrical preform by using an injection molding machine (M-100DM manufactured by Meiki) at a cylinder temperature of 275° C., a rotational speed of screw of 160 rpm, a primary pressure time of 3.0 sec. a mold temperature of 10° C. and a cycle time of 30 sec. The preform had an outer diameter of about 28 mm, an inner diameter of about 19 mm, a length of 136 mm and weight of about 56 g.

The obtained preform had an intrinsic viscosity of 0.68 and an AA content of 7.5 ppm, and it had excellent moldability and appearance.

Successively, after preheated by an infrared heater so that the surface temperature of the preform became about 110° C., the preform was treated for stretch blow molding by using a blow molding machine having set values of a blow pressure of 0.5 to 4.0 MPa and a mold temperature of 150° C. to obtain a PET bottle having an average thickness at the body of 330 µm and an inner volume of about 1.5 liters. The obtained PET bottle had a haze of 0.6% and a high quality, and it was recognized that the present invention enables the recycling of used PET bottles again to PET bottles.

Example 2

The wet TA cakes having a weight ratio of TA/water of about 83:12 obtained by cooling and solid-liquid separation after the hydrolysis reaction in Example 1 were charged into a nitrogen flow-type dryer at a speed of 95 pts. wt./hr by gravity feeding to treat them for drying. The water content of the dried TA powder was 0.2 wt. %. The TA powder was sent to a TA storing tank.

In the obtained TA powder, the concentrations of DMT and MMT were 500 ppm and 50 ppm, respectively, and the total content of 4-CBA, p-TA and BA was 30 ppm. Further, the 250° C. heat-resistant alkali permeability was 99.8% or more, and the TA was suitable as a raw material of PET for bottles.

Subsequently, into a TA slurry tank was charged the TA at a speed of 83 pts. wt./hr from the TA storing tank, and further EG at a speed of 50 pts. wt./hr. They were stirred to produce a slurry. Subsequently, the TA/EG slurry was supplied from the TA slurry tank to an esterification tank at a supply speed of 133 pts. wt./hr, and an esterification reaction was carried out under stirring at 270° C. while distilling out EG and water under such a condition that the retention time became 2 hr. The distilled-out EG was used to the depolymerization reaction after treating by distillation together with the other EG generated in the processes of the present invention. The water was subjected to a waste water treatment together with other generated water. The PET oligomer obtained in an esterification tank was supplied to an initial polymerization tank at a speed of 102 pts. wt./hr, and at the same time, a $Ge_2O_3$ (germanium oxide) catalyst was supplied at a speed of 0.015 pt. wt./hr, and a polycondensation reaction was carried out in a weak vacuum of 2 kPa at 280° C. under stirring while removing EG by distillation. The distilled-out EG was partially recycled to the depolymerization reaction after it was purified through a distillation treatment together with other EG.

The PET oligomer was supplied from the initial polymerization tank to a latter-term polymerization tank at a supply speed of 97 pts. wt./hr, and in the latter-term polymerization tank, a polycondensation reaction was curried out in a high vacuum of 0.13 kPa at 280° C. under stirring while distilling out EG to obtain a PET polymer. The intrinsic viscosity of the PET polymer was 0.51. The PET polymer was taken out from the latter-term polymerization tank in a molten state, cooled in a cooling bath and subsequently cut by a cutter into pellets. The pellets were supplied to a solid-phase polymerization tank at a supply speed of 96.5 pts. wt./hr. The solid-phase polymerization tank was a packed-type polymerizer furnished with a preliminary crystallizer. The solid phase polymerization reaction was carried out in a vacuum of 0.65 kPa while controlling a jacket temperature so that the temperature of the pellets in the center of the tank was kept at 210° C. under such a condition that the retention time in the tank was about 8 hr. The obtained PET polymer had an intrinsic viscosity of 0.76, a content of AA of 3.5 ppm and a content of oligomers of 0.3 ppm.

The PET polymer was the most suitable as a polymer for PET bottles. Further, the polymer was sent from the solid-phase polymerization tank to a PET storing tank at a speed of 96.4 pts. wt./hr to store it there. Subsequently, after dried for 5 hr at 160° C. in a vacuum dryer, the obtained chips were subjected to an injection molding to obtain a cylindrical preform by using an injection molding machine (M-100DM manufactured by Meiki) at a cylinder temperature of 275° C., a rotational speed of screw of 160 rpm, a primary pressure time of 3.0 sec, a mold temperature of 10° C. and a cycle time of 30 sec. The obtained preform had an outer diameter of about 28 mm, an inner diameter of about 19 mm, a length of 136 mm and weight of about 56 g.

The preform had an intrinsic viscosity of 0.67 and an AA content of 12 ppm, and it had excellent moldability and appearance.

Successively, after preheated by an infrared heater so that the surface temperature of the preform became about 110° C., the preform was subjected to stretch blow molding to obtain PET bottles. The molding was performed by using a blow molding machine at set values of a blow pressure of 0.5 to 4.0 MPa and a mold temperature of 150° C. The obtained PET bottle had an average thickness at the body of 330 µm and an inner volume of about 1.5 liters. The bottle had a haze of 0.5% and a high quality, and it was recognized that the present invention enables the recycling of used PET bottles again to PET bottles.

Reference Example 1

Except that the average size of crushed flakes in Example 1 was made 100 mm by adjusting the aperture of the screen of the crusher, the operation conditions were same as in Example 1. Resultingly, the transportation efficiency in the pneumatic transportation of the crushed flakes was lowered, and the electric load of the blower for the transportation was increased. Further, when the depolymerization product of completed reaction was treated by a solid-liquid separator, the amount of solids remained on the metal net was increased. The analysis of the composition of the solids revealed that the amount increased from the solids in Example 1 was attributable to the PET of the unreacted product in the depolymerization process. Accordingly, the recovery ratio of the product was decreased.

Reference Example 2

After unpacking a bale of PET bottles, the PET bottles were charged into the crusher, and they were crushed by using a screen whose aperture was set at 10 mm as in Example 1. However, the crushed products were not subjected to a winnower, not passed through the washing and gravity sorting process, that is, the contents of the bottles were not washed out with water, and foreign plastics were not removed by gravity separation, and the flakes which had only been made small pieces were used as the recovered PET flakes. Except this, Reference Example 2 was carried out under same conditions as in Example 1.

The recovered DMT was analyzed in the same manner as in Example 1. On the analysis of organic impurities by gas chromatography, a number of impurities which could not be identified were detected. The chlorine concentration in the DMT was 20 ppm, and the obtained DMT in this reference example could not be referred to as a high-quality DMT.

Further, the 250° C. heat-resistant alkali permeability was poor, and it was 93%.

Furthermore, the haze of the PET bottles manufactured by the same method as in Example 1 was poorly 2.5%. When compared with Example 1, the intrinsic viscosity was largely lowered, there was the deterioration of the transparency, and totally the color tone was pale yellow. The quality of the PET was so poor that the PET could not be used for PET bottles.

Reference Example 3

Except that the depolymerization reaction was carried out at a temperature of 220° C., the operation conditions were same as in Example 1. The recovered DMT was analyzed in the same manner as in Example 1, and the content of chlorine was 15 ppm, and a number of impurities which could not be identified were detected in the analysis of organic impurities by gas chromatography. Accordingly, the obtained DMT in this reference example could not be referred to as a high-quality DMT.

Further, the 250° C. heat-resistant alkali permeability was also poor, and it was 85%.

Furthermore, the haze of the PET bottles manufactured by the same method as in Example 1 was 2.5%. When compared with Example 1, the intrinsic viscosity was largely lowered, there was the deterioration of the transparency, and totally the color tone was pale yellow. The quality of the PET was so poor that the PET could not be used for PET bottles.

Reference Example 4

Except that after the completion of the ester interchange reaction, the recrystallization was not carried out, the operation conditions were same as in Example 1. The recovered DMT was analyzed in the same manner as in Example 1, and the content of an isomer impurity consisting of dimethyl isophthalate (DMI) was 800 ppm.

Successively, processes after hydrolysis were carried out in the same manner as in Example 1 to obtain a preform having an intrinsic viscosity of 0.66. Further, blow moldering was carried out as in Example 1 to obtain bottles having a haze of 2.0%. Further, a crystallization speed during the molding decreased, so that bottles having a sufficient strength and heat stability could not be obtained.

Reference Example 5

Except that the DMT distillation was omitted in the process of DMT recovery, the operation conditions were same as in Example 1. The recovered DMT was analyzed in the same manner as in Example 1, and the content of chlorine was 5 ppm, and a number of impurities which could not be identified were detected by gas chromatography. Accordingly, the obtained DMT in this reference example was not referred to as a high-quality DMT. Further, slight nasty smell was detected in the DMT.

Further, the 250° C. heat-resistant alkali permeability of the TA obtained through hydrolysis was poor, and it was 90%.

Furthermore, the haze of the PET bottle manufactured by the same method as in Example 1 was poorly 2.5%.

Reference Example 6

Except that the reaction temperature of the hydrolysis reaction was 180° C., the operation conditions were same as in Example 1. Resultingly, the concentrations of MMT and DMT in the TA were 1300 ppm and 180 ppm, respectively.

By using the TA, the polymerization process was carried out in the same manner as in Example 1, but the reactivity was low, so that it needed longer time than usual to reach the objective intrinsic viscosity, and the pellets were totally pale yellow. Their quality was so poor that they could not be used for PET bottles.

Reference Example 7

Except that the molar ratio of TA/EG in the slurry preparation tank was 1:5, the operation conditions were same as in Example 1. Resultingly, the DEG content in the obtained pellets was high, and it was 4.3 wt. %. The pellets were totally pale yellow, and had extremely lowered heat resistance, and the pellets had such a poor quality that they could not be used for PET bottles.

INDUSTRIAL FIELD OF APPLICATION

According to the present invention, a through process which comprises obtaining a high-quality terephthalic acid from recovered used PET bottles via dimethyl terephthalate, and obtaining a PET polymer for PET bottles by using the terephthalic acid as a raw material, enables the effective recycling of PET bottles, which receive special attention even among wastes due to their bulkiness and are becoming social issue.

The invention claimed is:

1. A method for recycling PET bottles characterized in that the wastes of resin bottles containing polyethylene terephthalate (PET) as the main component and further containing components different from it are passed sequentially through the following Processes (1) to (17):
   (1) a process for unpacking a packed bale of PET bottles which have been recovered through collection of classified refuse,
   (2) a process for removing iron and aluminum by a metal detector from the unpacked PET bottles, and subsequently crushing the PET bottles into flakes of 2-30 mm in sizes,
   (3) a process for separating polymer components different from PET consisting of polyethylene (PE), polystyrene (PS), polyvinyl chloride (PVC) from flaky pieces of PET bottles by winnowing,
   (4) a process for washing and gravity sorting having both the roles of washing out foreign materials attached inside and outside the crushed PET bottle pieces with water, and further removing sands, stones having specific gravities larger than water and PET, and foreign plastics having specific gravity smaller than water,
   (5) a depolymerization process for producing bis-β-hydroxyethyl terephthalate (BHET) by charging recovered PET flakes into ethylene glycol (EG) containing a PET depolymerization catalyst and treating the mixture at a temperature of 175-190° C. under a pressure of 0.1-0.5 MPa,
   (6) a solid-liquid separation process for removing solid foreign materials which have not dissolved in the above reaction solution,
   (7) a BHET concentration process for distilling and concentrating a solution fraction which has passed the solid-liquid separation process,
   (8) an ester interchange-recrystallization process for forming crude dimethyl terephthalate (DMT) and EG through an ester interchange reaction of the concentrated BHET in methanol (MeOH) in the presence of an ester interchange reaction catalyst, and subjecting the reaction mixture to recrystallization in a MeOH solvent, (9) a DMT distillation process for removing MeOH by distillation from the crude DMT to purify the DMT,

(10) a hydrolysis process for subjecting the purified DMT obtained in the DMT distillation process to a hydrolysis reaction together with water which is supplied in an amount 0.5 to 5 times the weight of the DMT at a temperature of 230-250° C. to produce terephthalic acid (TA),

(11) a process for cooling an aqueous slurry of the TA obtained in the hydrolysis process,

(12) a process for obtaining TA cakes from the cooled aqueous slurry of TA through solid-liquid separation,

(13) a slurry adjusting process in which the TA cakes obtained in Process (12) are added to a slurry preparation tank after the TA cakes are dried, and the mole ratio of TA/EG is adjusted to a range of 1:1 to 1:3,

(14) a process in which TA cakes and EG are made to perform an esterification reaction to obtain a PET oligomer,

(15) an initial melt-polycondensation process in which a polycondensation reaction catalyst and a stabilizer are added to the PET oligomer, the mixture is subjected to a melt polycondensation reaction in a weak vacuum of 1.3 kPa to 4.0 kPa at 260-300° C. to remove EG, and thus the degree of polymerization is increased,

(16) a latter term melt-polycondensation process in which the product of the previous process is further subjected to a melt polycondensation in a high vacuum of 67 Pa to 0.7 kPa at 270-300° C. to remove EG by distillation, and thus the degree of polymerization is further increased, and

(17) a solid phase polymerization process for further increasing the degree of polymerization in order to obtain a PET suitable for bottles.

2. A recycling method described in claim 1 in which the depolymerization catalyst to be used in Process (5) is at least one kind of compound selected from the group consisting of alkali metal carbonate salts, alkali metal hydrogencarbonate salts, alkali metal hydroxides, alkali metal alkoxides, alkaline earth metal carbonate salts, alkaline earth metal hydrogencarbonate salts, alkaline earth metal hydroxides, alkaline earth metal alkoxides, manganese acetate and zinc acetate.

3. A recycling method described in claim 1 in which the quantity of the addition of the depolymerization catalyst to be used in Process (5) is 0.1 to 10 wt.% based on the weight of recovered PET flakes.

4. A recycling method described in claim 1 in which the ester interchange reaction catalyst to be used in Process (8) is at least one kind of compound selected from the group consisting of alkali metal carbonate salts, alkali metal hydrogencarbonate salts, alkali metal hydroxides, alkali metal alkoxides, alkaline earth metal carbonate salts, alkaline earth metal hydrogencarbonate salts, alkaline earth metal hydroxides, alkaline earth metal alkoxides, manganese acetate and zinc acetate.

5. A recycling method described in claim 1 in which the quantity of addition of the ester interchange reaction catalyst to be used in Process (8) is 0.1 to 10 wt.% based on the weight of the recovered PET flakes.

6. A recycling method described in claim 1 in which the water content of the EG slurry in Process (13) is in the range of 0.1 to 20 wt.% based on the weight of EG.

7. A recycling method described in claim 1 in which the TA to be supplied to Process (14) has a total content of 4-carboxybenzaldehyde (4-CBA), methyl paratoluate (p-TA), benzoic acid (BA) and dimethyl hydroxyterephthalate of 1 ppm or less, and a total content of monomethyl terephthalate (MMT) and dimethyl terephthalate (DMT) in the range of 1 to 5000 ppm.

8. A recycling method described in claim 1 in which the polycondensation reaction catalyst to be used in Process (15) is at least one kind of compound selected from the group consisting of germanium compounds, antimony compounds and titanium compounds, and the stabilizer to be added is at least one kind of compound selected from the group consisting of phosphoric esters, phosphorous esters, acidic phosphoric acid esters, and phosphorus compounds.

9. A recycling method described in claim 1 in which the addition quantity of the polycondensation reaction catalyst to be used in Process (15) is 0.002 to 0.1 wt.% of the weight of the TA supplied in Process (14).

10. A recycling method described in claim 8 in which the polycondensation reaction catalyst is amorphous germanium dioxide, and the amount of the catalyst in the reaction is 20 to 150 ppm in terms of germanium element based on the TA.

11. A recycling method described in claim 8 in which the polycondensation reaction catalyst is antimony trioxide, and the amount of the catalyst in the reaction is 100 to 400 ppm in terms of antimony element based on the TA.

12. A recycling method described in claim 8 in which the polycondensation reaction catalyst is titanium tetrabutoxide, and the amount of the catalyst in the reaction is 1 to 100 ppm in terms of titanium element based on the TA.

13. A recycling method described in claim 8 in which the polycondensation reaction catalyst is titanium trimellitate, and the amount of the catalyst in the reaction is 1 to 100 ppm in terms of titanium element based on the TA.

14. A recycling method described in claim 8 in which the polycondensation reaction catalyst is a reaction product of titanium tetrabutoxide and mono-n-butyl phosphate, and the amount of the catalyst in the reaction is 1 to 100 ppm in terms of titanium element based on the TA.

15. A recycling method described in claim 8 in which the polycondensation reaction catalyst is a reaction product of titanium trimellitate and mono-n-butyl phosphate, and the amount of the catalyst in the reaction is 1 to 100 ppm in terms of titanium element based on the TA.

16. A recycling method described in claim 8 in which the polycondensation reaction catalyst is a reaction product of titanium tetrabutoxide and phenylphosphonic acid, and the amount of the catalyst in the reaction is 1 to 100 ppm in terms of titanium element based on the TA.

17. A recycling method described in claim 8 in which the polycondensation reaction catalyst is a reaction product of titanium trimellitate and phenylphosphonic acid, and the amount of the catalyst in the reaction is 1 to 100 ppm in terms of titanium element based on the TA.

18. A recycling method described in claim 8 in which the phosphoric esters are selected from the group consisting of trimethyl phosphate, triethyl phosphate and triphenyl phosphate, the phosphorous esters are selected from the group consisting of triphenyl phosphite and trisdodecyl phosphite, the acidic phosphoric acid esters are selected from the group consisting of methyl acid phosphate, dibutyl phosphate and monobutyl phosphate, and the phosphorus compounds are selected from the group consisting of phosphoric acid, phosphorous acid, hypophosphorous acid and polyphosphoric acid.

* * * * *